United States Patent
Kang (10) Patent No.: US 10,324,033 B2
(45) Date of Patent: Jun. 18, 2019

(54) IMAGE PROCESSING APPARATUS AND METHOD FOR CORRECTING AN ERROR IN DEPTH

(71) Applicant: SAMSUNG ELECTRONICS CO., LTD., Suwon-si, Gyeonggi-do (KR)

(72) Inventor: Byong Min Kang, Yongin-si (KR)

(73) Assignee: SAMSUNG ELECTRONICS CO., LTD., Gyeonggi-Do (KR)

(*) Notice: Subject to any disclaimer, the term of this patent is extended or adjusted under 35 U.S.C. 154(b) by 340 days.

(21) Appl. No.: 13/935,817

(22) Filed: Jul. 5, 2013

(65) Prior Publication Data

US 2014/0022349 A1    Jan. 23, 2014

Related U.S. Application Data

(60) Provisional application No. 61/673,979, filed on Jul. 20, 2012.

(30) Foreign Application Priority Data

Mar. 28, 2013   (KR) ......................... 10-2013-0033398

(51) Int. Cl.
| | |
|---|---|
| *G01N 21/55* | (2014.01) |
| *G01S 17/89* | (2006.01) |
| *G01S 7/481* | (2006.01) |
| *G01S 7/486* | (2006.01) |
| *H04N 5/3745* | (2011.01) |

(52) U.S. Cl.
CPC ............ *G01N 21/55* (2013.01); *G01S 7/4816* (2013.01); *G01S 7/4863* (2013.01); *G01S 17/89* (2013.01); *H04N 5/37452* (2013.01)

(58) Field of Classification Search
CPC ...... G01N 2223/506; G01S 21/55; G01S 7/89; G01S 7/4816; G01S 7/4863; G01S 5/37452
See application file for complete search history.

(56) References Cited

U.S. PATENT DOCUMENTS 6,373,557 B1 *   4/2002   Mengel .................. B60N 2/002
                                                                  356/4.07
7,330,028 B2    2/2008   Zhao et al.
(Continued)

FOREIGN PATENT DOCUMENTS

| EP | 0212737 | 3/1994 |
|---|---|---|
| JP | 2008-145263 | 6/2008 |

(Continued)

OTHER PUBLICATIONS

Office Action for Korean Patent Application No. 10-2013-0033398 dated Apr. 9, 2019 and English translation thereof.

*Primary Examiner* — Gims S Philippe
*Assistant Examiner* — Stefan Gadomski
(74) *Attorney, Agent, or Firm* — Harness, Dickey & Pierce, P.L.C.

(57) ABSTRACT

An image processing apparatus includes a light receiver to transduce a light reflected from an object into an electron corresponding to an intensity of the light, a measurer to measure quantities of charge on the electron with respect to at least two different divided time sections of an integration time section for acquiring a depth image, and an image generator to generate a depth image using at least one of the at least two measured quantities of charge on the electron.

11 Claims, 10 Drawing Sheets

(56) References Cited

U.S. PATENT DOCUMENTS

| | | | |
|---|---|---|---|
| 7,436,496 B2 | 10/2008 | Kawahito | |
| 7,907,257 B2 | 3/2011 | Lamesch et al. | |
| 2001/0046317 A1* | 11/2001 | Kamon | G01B 11/25 382/154 |
| 2005/0051707 A1* | 3/2005 | Bamji | G01C 3/08 250/214 R |
| 2008/0079833 A1* | 4/2008 | Ichikawa | G01S 7/4816 348/311 |
| 2008/0237445 A1* | 10/2008 | Ikeno | G01S 17/32 250/205 |
| 2009/0014658 A1* | 1/2009 | Cottier | H01L 27/14601 250/370.08 |
| 2009/0072170 A1* | 3/2009 | Kurihara | G01S 17/87 250/559.29 |
| 2009/0079955 A1* | 3/2009 | Tsunesada | G01S 17/89 356/4.01 |
| 2009/0152664 A1* | 6/2009 | Klem | H01L 27/14603 257/440 |
| 2009/0195770 A1* | 8/2009 | Satzky | G01S 7/4865 356/5.01 |
| 2010/0128129 A1* | 5/2010 | Kim | H04N 5/2226 348/164 |
| 2010/0142815 A1* | 6/2010 | Sim | G01S 7/497 382/167 |
| 2012/0013887 A1* | 1/2012 | Xu | G01S 17/89 356/4.02 |
| 2012/0059625 A1* | 3/2012 | Kim | G01B 11/026 702/159 |
| 2012/0098935 A1* | 4/2012 | Schmidt | G01S 17/89 348/46 |
| 2012/0188420 A1* | 7/2012 | Black | H04N 5/2253 348/279 |
| 2013/0056618 A1* | 3/2013 | Kurihara | H04N 5/37213 250/208.1 |
| 2013/0088620 A1* | 4/2013 | Centen | G01S 7/4863 348/273 |
| 2013/0228691 A1* | 9/2013 | Shah | H01L 27/14614 250/341.8 |
| 2013/0234029 A1* | 9/2013 | Bikumandla | H01L 25/043 250/349 |
| 2013/0307968 A1* | 11/2013 | Forster | G01S 7/497 348/135 |
| 2013/0329234 A1* | 12/2013 | Murakami | G01S 7/4912 356/625 |
| 2014/0078459 A1* | 3/2014 | Kim | G02F 1/1333 349/193 |

FOREIGN PATENT DOCUMENTS

| | | |
|---|---|---|
| JP | 2008-175538 | 7/2008 |
| JP | 4238322 | 3/2009 |
| JP | 4280822 | 6/2009 |
| JP | 2010-25906 | 2/2010 |
| JP | 2011-123071 | 6/2011 |
| JP | 2011-530706 | 12/2011 |
| KR | 10-2010-0064031 | 6/2010 |
| KR | 10-2011-0011244 | 2/2011 |
| KR | 10-2011-0044862 | 5/2011 |
| KR | 10-2012-0000299 A | 1/2012 |

* cited by examiner

| COLOR INDEX | INTEGRATION TIME 1 ($T_1$) | INTEGRATION TIME 2 ($T_2$) |
|---|---|---|
| | | |

# IMAGE PROCESSING APPARATUS AND METHOD FOR CORRECTING AN ERROR IN DEPTH

CROSS-REFERENCE TO RELATED APPLICATIONS

This application claims the benefit of U.S. Provisional Application No. 61/673,979, filed on Jul. 20, 2012, in the U.S. Patent and Trademark Office, and the benefit of Korean Patent Application No. 10-2013-0033398, filed on Mar. 28, 2013, in the Korean Intellectual Property Office, the entire disclosures of which are incorporated herein by reference for all purposes.

BACKGROUND

1. Field

Example embodiments disclosed herein relate to an image processing apparatus and method, and more particularly, to an apparatus and method for correcting an error in depth caused by saturation when a depth image is acquired.

2. Description of the Related Art

In general, a depth image of an object may be acquired using a time of flight (TOF) scheme.

The TOF scheme refers to a scheme of measuring a period of time taken for a light to be reflected and returned, after being radiated to an object using a TOF sensor. The TOF scheme is mainly used for generating a depth image in real time since a relatively smaller amount of time is used for measuring the period of time.

In a case of the TOF sensor, an error in accuracy may occur depending on a color of the object. For example, when the object has a bright color of which a reflectance is relatively high, for example, a reddish color, depth data of a generated depth image may be distorted due to saturation of a quantity of charge located on an electron transduced from the reflected light.

SUMMARY

The foregoing and/or other aspects may be achieved by providing an image processing apparatus, including a light receiver to transduce a light reflected from an object onto an electron corresponding to an intensity of the light, a measurer to measure quantities of charge on the electron with respect to at least two different divided time sections of an integration time section for acquiring a depth image, and an image generator to generate a depth image using at least one of the at least two measured quantities of charge on the electron.

The at least two different divided time sections may have different scales on a time axis. The scales of the at least two different divided time sections may be determined based on values obtained from a lookup table.

The image processing apparatus may further include a charge storage to store the transduced electron, and the measurer may detect whether a quantity of charge on the stored electron exceeds a predetermined threshold.

When the measurer detects that the quantity of charge on the stored electron exceeds the predetermined threshold, the image generator may generate the depth image using a quantity of charge measured in a divided time section of a smallest scale, among the at least two different divided time sections.

When the quantity of charge on the stored electron is less than the predetermined threshold, the image generator may generate the depth image using a sum of the quantities of charge on the electron measured with respect to the at least two different divided time sections.

The predetermined threshold may correspond to a function of capacitance of the charge storage.

The image processing apparatus may correspond to a time of flight (TOF) type.

The foregoing and/or other aspects may be achieved by providing an image processing apparatus, including a light receiver to transduce a light reflected from an object into an electron corresponding to an intensity of the light, a table in which at least two different divided time sections of an integration time section for acquiring a depth image corresponding to a color index of the object are predefined, a measurer to measure a quantity of charge with respect to a predetermined divided time section corresponding to the color index of the object, by referring to the table, and an image generator to generate a depth image using the measured quantity of charge.

The foregoing and/or other aspects may be achieved by providing an image processing method, including transducing a light reflected from an object into an electron corresponding to an intensity of the light, measuring quantities of charge on the electron with respect to at least two different divided time sections of an integration time section for acquiring a depth image, and generating a depth image using at least one of the at least two measured quantities of charge on the electron.

The at least two different divided time sections may have different scales on a time axis. The method may further include determining scales of the at least two different divided time sections by referring to a lookup table.

The measuring may include storing the transduced electron, and detecting whether a quantity of charge on the stored electron exceeds a predetermined threshold.

The generating may include generating the depth image using a quantity of charge measured in a divided time section of a smallest scale, among the at least two different divided time sections, when the quantity of charge on the stored electron exceeds the predetermined threshold.

The generating may include generating the depth image using a sum of the quantities of charge on the electron measured with respect to the at least two different divided time sections when the quantity of charge on the stored electron is less than the predetermined threshold.

The foregoing and/or other aspects may be achieved by providing an image processing method, including transducing a light reflected from an object into an electron corresponding to an intensity of the light, measuring a quantity of charge with respect to a predetermined divided time section corresponding to a color index of the object, by referring to a table in which at least two different divided time sections of an integration time section for acquiring a depth image corresponding to the color index of the object are predefined, and generating a depth image using the measured quantity of charge.

The foregoing and/or other aspects may be achieved by providing an image processing method, including transducing a light reflected from an object into an electron corresponding to an intensity of the light, dividing an integration time into at least two divided time sections, a duration of each divided time section being determined by referring to a table, measuring quantities of charge on the electron with respect to the at least two divided time sections, determining whether a measured quantity of charge with respect to the at least two divided time sections, exceeds a predetermined threshold, and generating a depth image based on the determination.

The table may include color index information of an object and duration information for the at least two divided time sections corresponding to the color index. A first divided time section may have a longer duration than a second divided time section. The at least two divided time sections may be defined based on whether a reflectance value exceeds a predetermined threshold or based on a type of color of the object.

A non-transitory computer-readable medium may include a program for instructing a computer to perform any one of the image processing methods described above.

Additional aspects of embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of embodiments, taken in conjunction with the accompanying drawings of which.

DETAILED DESCRIPTION

Reference will now be made in detail to embodiments, examples of which are illustrated in the accompanying drawings, wherein like reference numerals refer to like elements throughout. Embodiments are described below to explain the present disclosure by referring to the figures.

The terms used herein are mainly selected from general terms currently being used in light of functions in the present disclosure. However, the meanings of the terms used herein may be changed to conform to or accommodate the intent of an operator in the art, a custom, or the appearance of new technologies.

In addition, in a specific case, most appropriate terms are arbitrarily selected by the applicant for ease of description and/or for ease of understanding. In this instance, the meanings of the arbitrarily used terms will be clearly explained in the corresponding description. Hence, the terms should be understood not by the simple names of the terms but by the meanings of the terms and the following overall description of this specification and/or in view of the accompanying drawings.

Figure 1A:
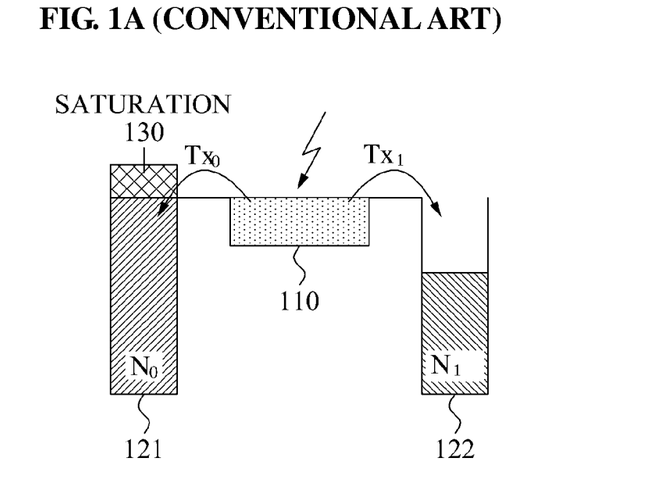
FIGS. 1A and 1B illustrate saturation occurring when a depth image is generated according to a conventional art.
Figure 1B:
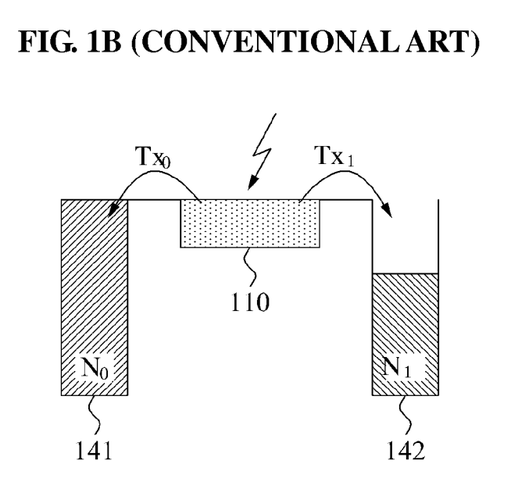

FIGS. 1A and 1B illustrate saturation occurring when a depth image is generated according to a conventional art.

When a depth image is generated using a time of flight (TOF) scheme, an error in accuracy may occur depending on a color of an object. In particular, when the object has a bright color, for example, a reddish color, an error may occur in the generated depth image.

The error may be caused by saturation of a TOF sensor.

In general, an equation for computing depth data when a depth image is generated may be expressed by Equation 1.

$$R = \frac{c}{2} T_{TOF} = \frac{cT_{on}}{2} \cdot \frac{N_1}{N_0 + N_1} \quad \text{[Equation 1]}$$

In Equation 1, c denotes a speed of light, for example, $3.0 \times 10^8$ meters per second (m/s), and $T_{on}$ denotes a time for radiating a light source to the object during a duty cycle of a modulation frequency.

In addition, R denotes a distance of the object, $T_{TOF}$ denotes a time taken for a light to be reflected and returned after being radiated to an object using the TOF sensor, $N_0$ denotes a quantity of charge stored in a first charge storage 121, and $N_1$ denotes a quantity of charge stored in a second charge storage 122.

For example, when a modulation frequency corresponds to 10 megahertz (MHz) and a 50% duty cycle is used, $T_{on}$ may correspond to 50 nanoseconds (nsec) (e.g., ½*1/(10× $10^6$)), and the light source may be turned off for subsequent 50 nsec to modulate the radiated light.

Here, the light source may include a light emitting diode (LED).

The modulated radiated light may be received by the TOF sensor during an integration time. The TOF sensor may transduce the received light into an electron, and store the transduced electron in at least two storages.

Referring to FIG. 1A, a light received by a light receiver 110 may be transduced into an electron, and the transduced electron may be stored in two charge storages 121 and 122.

For example, the light receiver 110 may include a photodiode.

In FIG. 1A, $N_0$ denotes a quantity of charge stored in the first charge storage 121, and $N_1$ denotes a quantity of charge stored in the second charge storage 122. There may exist a limit to a quantity of charge to be stored, depending on respective capacities of the two charge storages 121 and 122.

For example, when a light, for example, in a near infrared range, reflected for 100 milliseconds (msec) from an object in a 0.75-meter (m) distance is received, $N_0$ may correspond to ninety thousand, and $N_1$ may correspond to ten thousand. In this instance, when a quantity of charge storable in the first charge storage 121 corresponds to eighty-five thousand, saturation 130 with respect to a quantity of charge corresponding to five thousand may occur. That is, the quantity of charge which may be stored in the first charge storage 121 is exceed by five thousand and the first charge storage 121 is saturated.

Due to the saturation 130, the saturated quantity of charge corresponding to five thousand may not be considered when the depth data for generating the depth image is computed, as shown in FIG. 1B. In this instance, $N_0$ corresponding to eighty-five thousand stored in first charge storage 141 and $N_1$ corresponding to ten thousand stored in second charge storage 142 may be used to compute the depth data using Equation 1. As a result, a distance corresponding to 0.79 m may be output. In this instance, an error between the calculated distance 0.79 m and the actual distance 0.75 m may correspond to 0.04 m.

In particular, an error corresponding to 0.04 m may occur in the depth data due to the limit to the quantity of charge storable in the first charge storage 141 and resulting saturation.

Figure 2:
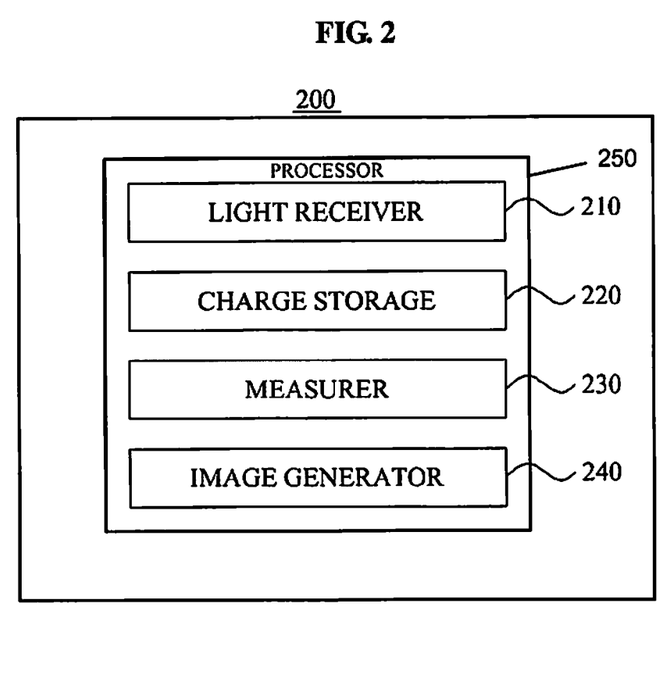
FIG. 2 illustrates an image processing apparatus according to example embodiments.

FIG. 2 illustrates an image processing apparatus 200 according to example embodiments.

Referring to FIG. 2, the image processing apparatus 200 may include a light receiver 210, a measurer 230, and an image generator 240 (or in an example embodiment, a processor 250 that executes computer readable instructions to implement functionalities of one or more of the light receiver 210, a charge storage 220, the measurer 230, and the image generator 2401.

The light receiver 210 may transduce a light reflected from an object into an electron corresponding to an intensity of the light.

The measurer 230 may measure quantities of charge on the transduced electron with respect to at least two different divided time sections of an integration time section for acquiring a depth image.

In this instance, the at least two different divided time sections may have different scales on a time axis.

The image generator 240 may generate a depth image using at least one of the at least two measured quantities measured by the measurer 230.

The image processing apparatus 200 may further include a charge storage 220 to store the electron transduced by the light receiver 210. Depending on implementation, when the image processing apparatus 200 is implemented in a form of a system on chip, the charge storage 220 may be disposed in a location physically spaced away from the image processing apparatus 200 (or other elements of the image processing apparatus such as the light receiver 210, measurer 230, and/or image generator 240).

The charge storage 220 may be configured by a predetermined capacitor means or device capable of accumulating corresponding electrons.

The measurer 230 may measure a quantity of charge on the electron stored in the charge storage 220, and detect whether the measured quantity of charge exceeds a predetermined threshold. The predetermined threshold may be expressed by a function of capacitance of the charge storage 220.

When the measurer 230 detects that the measured quantity of charge exceeds the predetermined threshold, the image generator 240 may generate the depth image using a quantity of charge measured in a divided time section of a smallest scale, among the at least two different divided time sections included in the integration time section for generating a depth image.

Conversely, when the measured quantity of charge is less than the predetermined threshold, the image generator 240 may generate the depth image using a sum of the quantities of charge measured with respect to the at least two different divided time sections included in the integration time section for generating a depth image.

As described above, the image processing apparatus 200 may employ a TOF scheme.

Figure 3A:
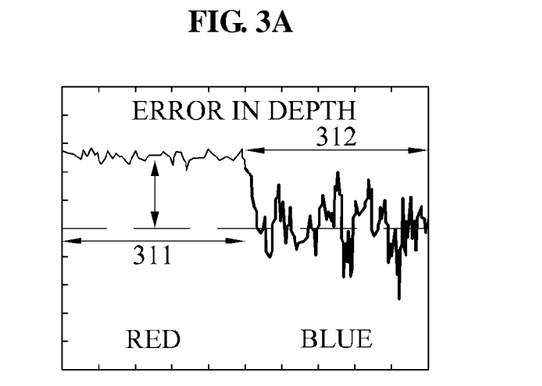
FIGS. 3A through 3C illustrate a scheme of determining a quantity of charge to be used for generating a depth image based on whether saturation occurs according to example embodiments.
Figure 3B:
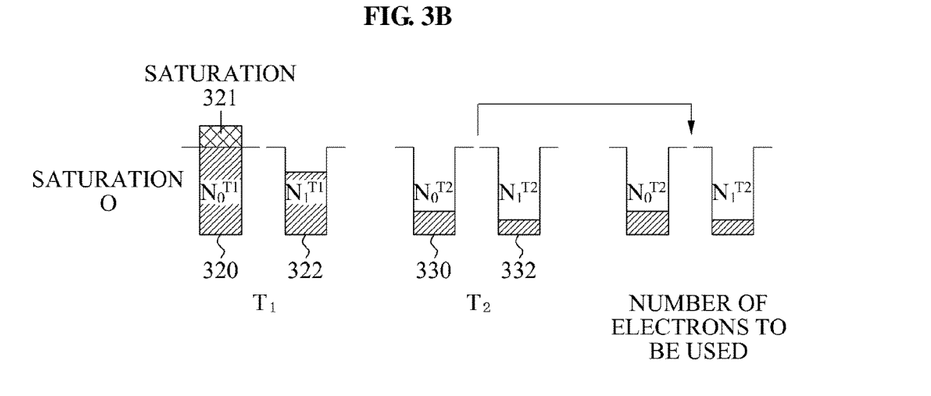
Figure 3C:
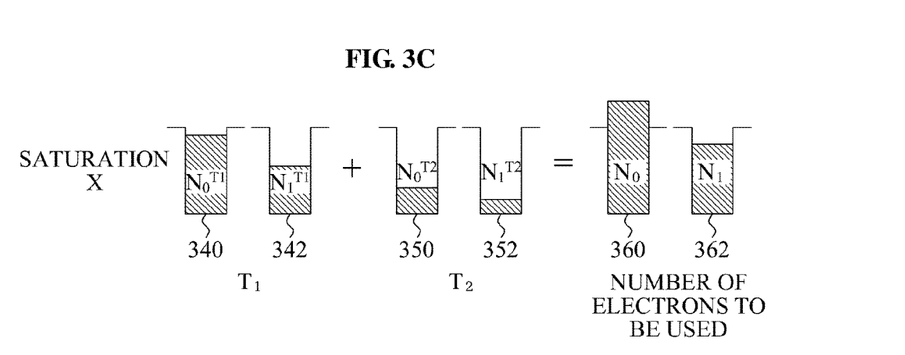

FIGS. 3A through 3C illustrate a scheme of determining a quantity of charge to be used for generating a depth image based on whether saturation occurs according to example embodiments.

In particular, FIG. 3A is a graph illustrating an error in depth data depending on colors.

In addition, FIG. 3B illustrates a quantity of charge to be used for generating a depth image when saturation occurs, and FIG. 3C illustrates a scheme of determining a quantity of charge to be used for generating a depth image when saturation does not occur.

Referring to FIG. 3A, when a color of an object corresponds to a bright color, for example, red 311, rather than blue 312, a relatively great error may occur when a depth image is generated since near infrared light may be mainly used as a light radiated from a light source.

The near infrared light may refer to a light having a wavelength band close to a wavelength band of red. For example, the color red may have a wavelength from about 620 nm to about 740 nm, while infrared light may have a wavelength from about 700 nm to about 1 mm. Thus, a portion of the infrared wavelength band may overlap or be approximate to the wavelength band of the color red. When a red object is provided, the near infrared light may be saturated rapidly since a great amount of light may be reflected and returned from the object, when compared to (relative to) an object in another color. Accordingly, in a case of a red and bright object, an error in depth data may occur due to rapid saturation, as shown in FIGS. 1A and 1B.

In order to correct an error in depth data caused by saturation, two methods may be employed.

A first method may correspond to a method of designing a charge storage of a TOF sensor to have a large capacity.

When the charge storage of the TOF sensor is designed to have a large capacity, a sensitivity may decrease, and a relative capacity of a light receiver configured to receive a light from a pixel may decrease, for example, due to a reduction of a fill factor, and the like. Accordingly, a relatively great decrease in an accuracy of the depth data may occur.

A second method may correspond to a method of reducing an integration time to be expended for acquiring a depth image of an object.

When the integration time is reduced, a number of electrons transduced from a light may decrease and thus, a relatively great decrease in an accuracy of the depth data may occur.

According to example embodiments, the image processing apparatus 200 may employ a scheme of increasing an accuracy of depth data by dividing the integration time, and generating a depth image using a quantity of charge stored in each divided time section.

As shown in FIGS. 3B and 3C, the integration time may be divided into two divided time sections $T_1$ and $T_2$, and a quantity of charge stored in each divided time section may be measured.

For example, when an integration time corresponding to a total time of 100 msec is used, the integration time may be divided into the time section $T_1$ corresponding to 80 msec and the time section $T_2$ corresponding to 20 msec, and quantities of charge of the transduced electron with respect to the two divided time sections $T_1$ and $T_2$ may be stored in the charge storage 220. The integration time may be divided into the time section $T_1$ and the time section $T_2$ using a predetermined ratio for each divided time section. The integration time may be divided into the time section $T_1$ and the time section $T_2$ where time section $T_2$ is less than $T_1$. The integration time may be dependent upon a color type or object type, or a combination thereof. The integration time may be divided into the time section $T_1$ and the time section $T_2$ wherein values for each of time section $T_1$ and the time section $T_2$ may be stored beforehand in a storage unit or a lookup table, as disclosed herein and explained further below.

Referring to FIG. 3B, saturation 321 may occur in the time section $T_1$, and saturation may not occur in the time section $T_2$. Here, quantities of charge 320 and 322 may be stored in a first charge storage and second charge storage, respectively, during time section $T_1$. Likewise, quantities of charge 330 and 332 may be stored in a first charge storage and second charge storage, respectively, during time section $T_2$. Accordingly, quantities 330 and 332 of charge measured in the time section $T_2$ may be used to compute depth data, since quantities 330 and 332 correspond to a divided time section of a smallest scale.

Since a probability that saturation occurs in the divided time section $T_1$ or $T_2$ may decrease, when compared to the integration time, depth data without an error may be computed with respect to all colors when a depth image is generated.

Referring to FIG. 3C, since saturation may not occur in both divided time sections $T_1$ and $T_2$, depth data may be computed using a sum of quantities 340 and 342 of charge measured in the time section $T_1$ and quantities 350 and 352 of charge measured in the time section $T_2$.

In particular, in FIG. 3C, quantities 360 and 362 of charge to be used for generating a depth image may be identical to a sum of the quantities 340 and 342 of charge measured in the time section $T_1$ and the quantities 350 and 352 of charge measured in the time section $T_2$.

As described above, the scheme performed by the image processing apparatus 200 for generating a depth image is directed to dividing an integration time into at least two divided time sections, measuring quantities of charge with respect to the at least two divided time sections, respectively, and generating a depth image using a quantity of charge measured in a divided time section determined based on whether saturation occurs. The embodiments described above are provided as examples only and thus, the present disclosure is not to be limited thereto.

Figure 4:
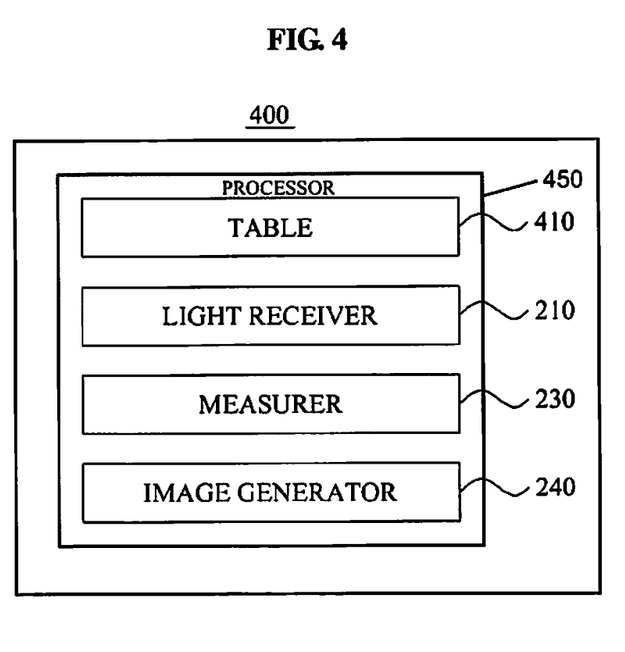
FIG. 4 illustrates an operation of an image processing apparatus according to example embodiments.

FIG. 4 illustrates an operation of an image processing apparatus 400 according to example embodiments.

A basic mechanism of the image processing apparatus 400 may be identical to the mechanism of the image processing apparatus 200 of FIG. 2. However, the image processing apparatus 400 may record information about a divided time section corresponding to a color of an object in a predetermined table in advance.

In particular, when a quantity of charge on an electron transduced from a light reflected from the object is measured, the information about the divided time section corresponding to the color of the object may be obtained by referring to the predetermined table. According to the present embodiments, an optimized divided time section for each color of the object may be predetermined, and information about a divided time section corresponding to a color of the object may be retrieved for use from the table.

Referring to FIG. 4, the image processing apparatus 400 may include a table 410, and the elements previously described with reference to FIG. 2, in particular, the light receiver 210, the measurer 230, and the image generator 240 (or in an example embodiment, a processor 450 that executes computer readable instructions to implement functionalities of one or more of the light receiver 210, the measurer 230, and the image generator 240).

The table 410 may be configured to record information about at least two different divided time sections of an integration time section for acquiring a depth image corresponding to a color index of an object. Information about a divided time section to be recorded in the table 410 may be predetermined mathematically or experimentally based on a color index of the object. When an update to the corresponding information is required, the information recorded in the table 410 may be updated by a scheme of a firmware update, and the like. The table 410 will be described in detail with reference to FIG. 5.

Figure 5:
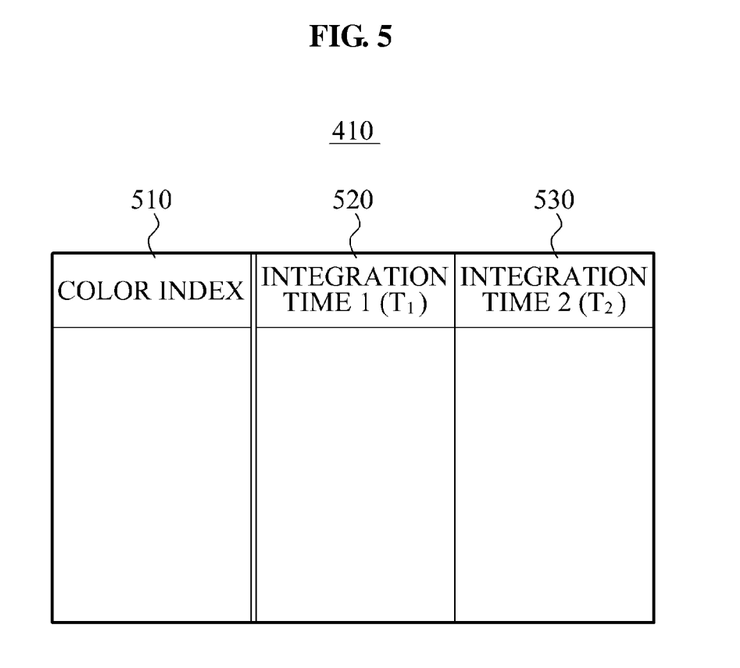
FIG. 5 illustrates a detailed configuration of a table of the image processing apparatus of FIG. 4.

FIG. 5 illustrates a detailed configuration of the table 410 of the image processing apparatus 400 of FIG. 4.

The table 410 may define an integration time section for acquiring a depth image corresponding to a color index of an object as at least two different divided time sections, and store the at least two different divided time sections for each color index. The table may be recorded or stored in a non-volatile memory device such as a read only memory (ROM), a random access memory (RAM), a programmable read only memory (PROM), an erasable programmable read only memory (EPROM), a flash memory, or a USB device, a volatile memory device such as a random access memory (RAM), or a storage medium such as a hard disk or optical disk. However, the present invention is not limited thereto.

Referring to FIG. 5, the table 410 may include a color index 510 associated with the object, a first divided time section $T_1$ 520, and a second divided time section $T_2$ 530. Here, the first divided time section $T_1$ 520 and the second divided time section $T_2$ 530 may be predefined for each color index. There may be a plurality of tables, each table corresponding to a specific object. Each table predefined for a specific object may include a color index including a predetermined number of colors corresponding to the specified object. Alternatively, a single table may be applied to a plurality of objects, with the color index including colors corresponding to each of the plurality of objects.

The color index 510 may be construed as at least one of a type of at least one color constituting the object, a reflectance corresponding to the at least one color, and color data of the object.

For example, when the color index 510 corresponds to the reflectance with respect to a color included in the object, the at least two different divided time sections 520 and 530 may be defined differently depending on whether the reflectance exceeds a predetermined threshold.

In addition, when the color index 510 corresponds to the type of at least one color constituting the object or the color data of the object, the first divided time section $T_1$ 520 and the second divided time section $T_2$ 530 may be defined, respectively, based on the type of at least one color or the color data.

Referring back to FIG. 4, the light receiver 210 may transduce a light reflected from the object into an electron corresponding to an intensity of the light.

The measurer 230 may measure a quantity of charge with respect to a divided time section corresponding to a color index of the object, by referring to the table 410.

The image generator 240 may generate a depth image using the measured quantity of charge. The image generator 240 may generate the depth image using a quantity of charge measured in a divided time section of a smallest scale, among the at least two different divided time sections included in the integration time section for generating a depth image, if the measurer 230 detects that the measured quantity of charge exceeds the predetermined threshold. Alternatively, if the measured quantity of charge is less than the predetermined threshold, the image generator 240 may generate the depth image using a sum of the quantities of charge measured with respect to the at least two different divided time sections included in the integration time section for generating a depth image.

Figure 6:
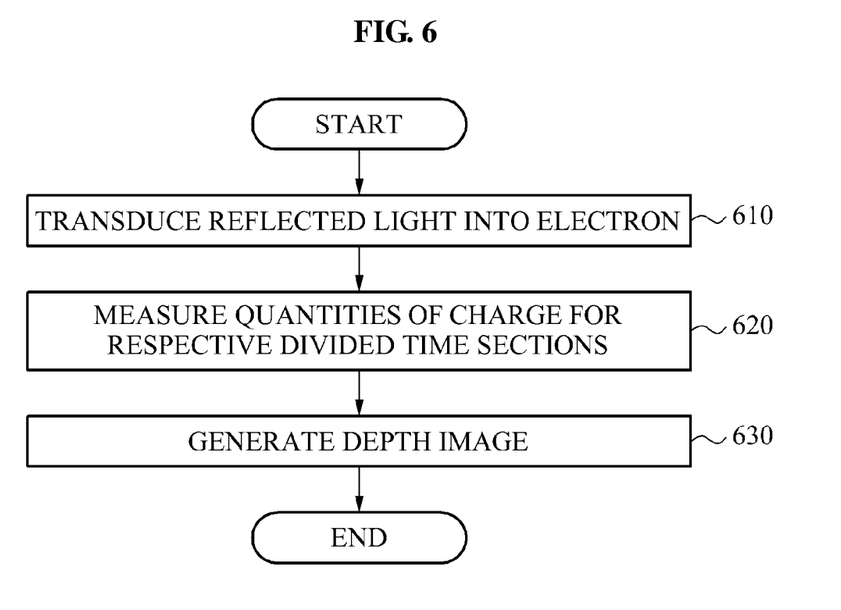
FIG. 6 illustrates an image processing method according to example embodiments.

FIG. 6 illustrates an image processing method according to example embodiments. The image processing method of FIG. 6 may be performed by the image processing apparatus 200 of FIG. 2.

Referring to FIG. 6, in operation 610, the light receiver 210 may transduce a light reflected from an object into an electron corresponding to an intensity of the light.

In operation 620, the measurer 230 may measure quantities of charge on the electron with respect to at least two different divided time sections of an integration time section for acquiring a depth image.

In this instance, the at least two different divided time sections may have different scales on a time axis.

In operation 630, the image generator 240 may generate a depth image using at least one of the at least two measured quantities of charge.

The image processing apparatus 200 may further include the charge storage 220 to store the electron transduced by the light receiver 210. The charge storage 220 may be configured or embodied by a predetermined capacitor means capable of accumulating corresponding electrons.

In particular, in operation 620, the measurer 230 may measure a quantity of charge on the electron stored in the charge storage 220, and detect whether the measured quantity of charge exceeds a predetermined threshold.

The predetermined threshold may be expressed by a function of capacitance of the charge storage 220.

In operation 630, the image generator 240 may generate the depth image using a quantity of charge measured in a divided time section of a smallest scale, among the at least two different divided time sections included in the integration time section for generating a depth image when the measurer 230 detects that the measured quantity of charge exceeds the predetermined threshold.

Conversely, in operation 630, the image generator 240 may generate the depth image using a sum of the quantities of charge measured with respect to the at least two different divided time sections included in the integration time section for generating a depth image, when the measured quantity of charge is less than the predetermined threshold.

A detailed description and various examples on the operations of FIG. 6 may be identical to the description and examples provided with reference to FIGS. 2 through 3C.

Figure 7:
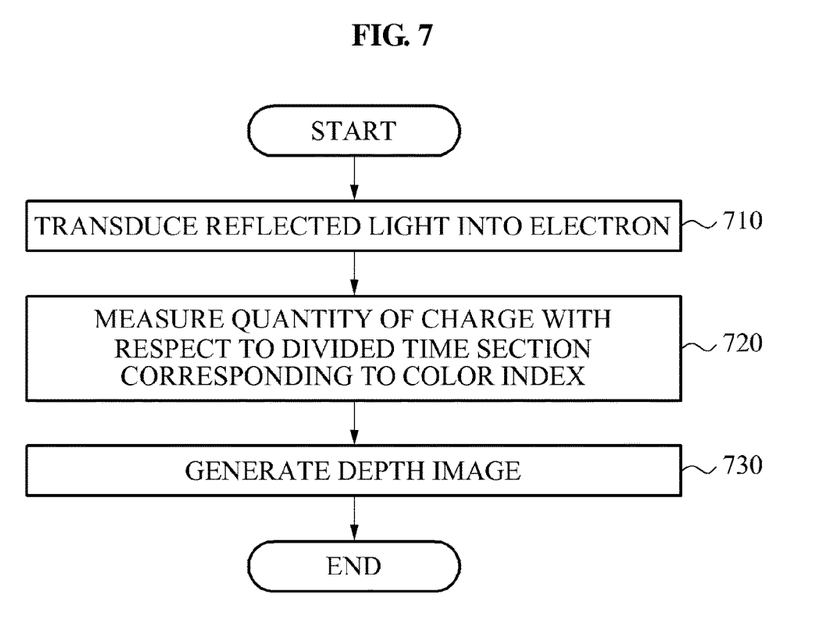
FIG. 7 illustrates an image processing method according to other example embodiments.

FIG. 7 illustrates an image processing method according to other example embodiments. The image processing method of FIG. 7 may be performed by the image processing apparatus 400 of FIG. 4.

Referring to FIG. 7, in operation 710, the light receiver 210 may transduce a light reflected from an object onto an electron corresponding to an intensity of the light.

In operation 720, the measurer 230 may measure a quantity of charge with respect to a divided time section corresponding to a color index of the object, by referring to the table 410.

The table 410 may define an integration time section for acquiring a depth image corresponding to a color index of the object as at least two different divided time sections, and store the at least two different divided time sections for each color index.

The color index may be construed as at least one of a type of at least one color constituting the object, a reflectance corresponding to the at least one color, and color data of the object.

In operation 730, the image generator 240 may generate a depth image using the measured quantity of charge. The image generator 240 may generate the depth image using a quantity of charge measured in view of the divided time sections obtained from the table. A divided time section having a smallest scale may be used, among the at least two different divided time sections included in the integration time section for generating a depth image, if the measurer 230 detects that the measured quantity of charge exceeds the predetermined threshold. Alternatively, if the measured quantity of charge is less than the predetermined threshold, the image generator 240 may generate the depth image using a sum of the quantities of charge measured with respect to the at least two different divided time sections included in the integration time section for generating a depth image.

A detailed description and various examples on the operations of FIG. 7 may be identical to the description and examples provided with reference to FIGS. 3A through 5.

The units described herein may be implemented using hardware components, software components, or a combination thereof. For example, a processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner.

The software may include a computer program, a piece of code, an instruction, or some combination thereof, for independently or collectively instructing or configuring the processing device to operate as desired.

The method according to the above-described embodiments may be recorded in non-transitory computer-readable media including program instructions to implement various operations embodied by a computer. The media may also include, alone or in combination with the program instructions, data files, data structures, and the like. Examples of non-transitory computer-readable media may include magnetic media such as hard discs, floppy discs, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described embodiments, or vice versa. The program instructions may be executed by one or more processors. In addition, a non-transitory computer-readable storage medium may be distributed among computer systems connected through a network and computer-readable codes or program instructions may be stored and executed in a decentralized manner. In addition, the computer-readable storage media may also be embodied in at least one application specific integrated circuit (ASIC) or Field Programmable Gate Array (FPGA).

Although a few embodiments have been shown and described, it would be appreciated by those skilled in the art that changes may be made to these embodiments without departing from the principles and spirit of the disclosure, the scope of which is defined by the claims and their equivalents. For example, suitable results may be achieved if the described techniques are performed in a different order and/or if components in a described system, architecture, device, or circuit are combined in a different manner and/or replaced or supplemented by other components or their equivalents.

Accordingly, other implementations, example embodiments, and equivalents to the claims are within the scope of the following claims.

What is claimed is:

1. An image processing apparatus, comprising:
a light sensor configured to convert light reflected from an object into charge carriers based on an intensity of the light; and
a processor configured to,
measure,
a first quantity of the charge carriers stored in a first charge storage during a first time section of at least two different time sections of an integration time section,
a second quantity of the charge carriers stored in the first charge storage during a second time section of the at least two different time sections of the integration time section,
a third quantity of the charge carriers stored in a second charge storage during the first time section, and
a fourth quantity of the charge carriers stored in the second charge storage during the second time section,
determine whether any of the first, second, third or fourth quantities of the charge carriers exceeds a threshold,
generate a depth image based on the quantities, from among the first through fourth quantities of the charge carriers, measured in one of the at least two different time sections having a smallest duration among the at least two different time sections in response to the processor determining that any of the first through fourth quantities of the charge carriers exceeds the threshold, and
generate the depth image based on a sum of the first and third quantities of the charge carriers and a sum of the second and fourth quantities of the charge carriers in response to the processor determining that none of the first through fourth quantities exceeds the threshold,
wherein the at least two different time sections have different durations on a time axis.

2. The image processing apparatus of claim 1, wherein the at least two different time sections are sequential.

3. The image processing apparatus of claim 1, wherein the threshold is a capacitance.

4. The image processing apparatus of claim 1, wherein the image processing apparatus is a time of flight (TOF) type.

5. The image processing apparatus of claim 2, wherein intervals of the at least two different time sections are based on values obtained from a lookup table, the values corresponding to a color index of the object.

6. An image processing apparatus, comprising:
a light sensor configured to convert light reflected from an object into charge carriers based on an intensity of the light;
a lookup table including values of at least two different time sections of an integration time section, the values corresponding to a color index of the object; and
a processor configured to,
measure,
a first quantity of the charge carriers stored in a first charge storage during a first time section of the at least two different time sections of an integration time section,
a second quantity of the charge carriers stored in the first charge storage during a second time section of the at least two different time sections of the integration time section,
a third quantity of the charge carriers stored in a second charge storage during the first time section, and
a fourth quantity of the charge carriers stored in the second charge storage during the second time section,
determine whether any of the first, second, third or fourth quantities exceeds a threshold,
generate a depth image based on the quantities, from among the first through fourth quantities of the charge carriers, measured in one of the at least two different time sections having a smallest duration among the at least two different time sections in response to the processor determining that any of the first through fourth quantities exceeds the threshold, and
generate the depth image based on a sum of the first and third quantities of the charge carriers and a sum of the second and fourth quantities of the charge carriers in response to the processor determining that none of the first through fourth quantities exceeds the threshold,
wherein the at least two different time sections have different durations on a time axis.

7. An image processing method, comprising:
converting a light reflected from an object into charge carriers based on an intensity of the light;
measuring,
a first quantity of the charge carriers stored in a first charge storage during a first time section of at least two different time sections of an integration time section,
a second quantity of the charge carriers stored in the first charge storage during a second time section of the at least two different time sections of the integration time section,
a third quantity of the charge carriers stored in a second charge storage during the first time section, and
a fourth quantity of the charge carriers stored in the second charge storage during the second time section,
determining whether any of the first, second, third or fourth quantities of the charge carriers exceeds a threshold; and
generating a depth image based on the quantities, from among the first through fourth quantities of the charge carriers, measured in one of the at least two different time sections having a smallest duration among the at least two different time sections in response to any of the first through fourth quantities of the charge carriers exceeding the threshold, and
generating the depth image based on a sum of the first and third quantities of the charge carriers and a sum of the second and fourth quantities of the charge carriers in response to none of the first through fourth quantities exceeding the threshold,
wherein the at least two different time sections have different durations on a time axis.

8. The image processing method of claim 7, wherein the at least two different time sections are sequential.

9. The image processing method of claim 8, further comprising:

determining intervals of the at least two different time sections by referring to a lookup table that includes values of at least two different time sections of an integration time section, the values corresponding to a color index of the object.

10. A non-transitory computer-readable medium comprising computer-readable instructions, which when executed by a processor, cause the processor to perform the method of claim 7.

11. The image processing apparatus of claim 1, wherein one of the at least two different time sections has an interval that is less than the other time section.

* * * * *